United States Patent [19]

Freeman

[11] 4,375,966
[45] Mar. 8, 1983

[54] SYSTEM FOR MAKING DIRECT ORAL IMPRESSION TRAY

[75] Inventor: Frank H. Freeman, Farmington, Mich.

[73] Assignee: Sybron Corporation, Rochester, N.Y.

[21] Appl. No.: 295,343

[22] Filed: Aug. 24, 1981

[51] Int. Cl.³ .............................................. A61L 9/00
[52] U.S. Cl. ...................................................... 433/37
[58] Field of Search ......................................... 433/37

[56] References Cited
U.S. PATENT DOCUMENTS 3,834,025  9/1974  Schunemann .................. 433/37
3,878,610  4/1975  Coscina ........................... 433/37

Primary Examiner—Robert Peshock
Attorney, Agent, or Firm—Robert A. Gerlach; Robert J. Bird

[57] ABSTRACT

A system and materials for making oral impression trays in situ is disclosed, including a transporter member, tray member, and spacer member. Materials are disclosed for use as mold materials for polymerization in situ against or in close proximity to living tissue without high exothermal polymerization and its attendant discomfort and damage and with reduced polymerization shrinkage to produce a more accurate and stable custom tray.

2 Claims, 6 Drawing Figures

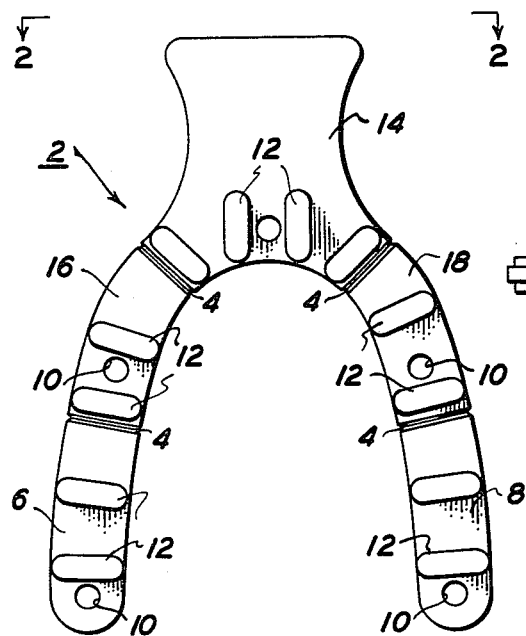
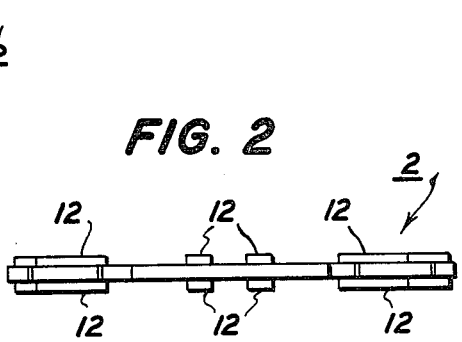
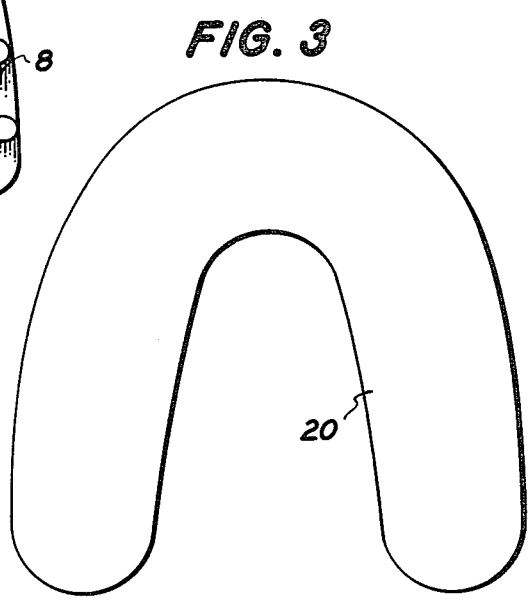
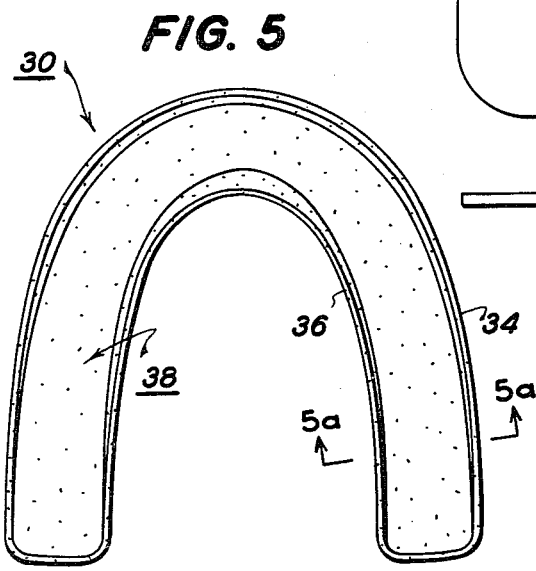
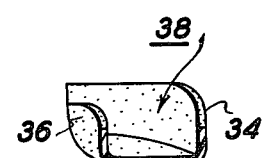

SYSTEM FOR MAKING DIRECT ORAL IMPRESSION TRAY

BACKGROUND OF THE INVENTION

The subject matter of this invention is oral impression trays, and devices and materials for making oral impression trays in situ.

In the prior art, oral impressions are taken by the dentist as a starting point in the fabrication of a variety of restorations and dental appliances. A number of impression material systems are available to meet the needs and varied skills of the dentists. Included in the list of available materials are a variety of elastomeric compositions based upon polysulfides, addition silicones, condensation silicones, polyethers and other elastomers. These materials typically are two-part systems, consisting of a "base" composition and a "catalyst" composition, which, when mixed, convert the fluid resin to an elastomer. When properly proportioned and mixed, the materials are carried into the oral cavity via some type of "tray." The trays may be reusable, of metal or plastic construction, and are designed to approximate the contour of either the mandibular or maxillary arch. They are usually provided in a series of sizes to permit a close approximation of fit to the oral area under consideration.

A similar variety of cheaper, less rigid disposable trays are also available to the dentist. These, again, only approximately fit the dental arch and, in general, are less structurally strong and rigid. All of these "standard" trays give only an approximate "fit" over the oral area of which an impression is needed. In some areas the trays may be nearly touching the oral tissues, and in other areas a considerable space may exist between the tray and the oral tissues. The variations in spacing result in a correspondingly varying bulk of impression material within the trays. This variation in material bulk contributes to inaccuracies in the oral impression and to waste of expensive impression material. Variations in tissue compression and variations in polymerization shrinkage are among the factors causing the inaccurate impressions.

In an effort to better control the tissue reactions and to optimize the stresses induced by the polymerization shrinkage of the impression material, the more discriminating dentist will use custom-made trays for taking impressions. This insures improved impression accuracy and minimizes future problems and remakes. Currently, custom trays are produced by an indirect (extra-oral) technique, as follows:

1. A "snap" impression is taken of the oral structure using a cheap impression material. The greatest accuracy is neither required nor sought.

2. An artificial stone model is poured into the "snap" impression and allowed to harden for approximately one hour. This model is thus a positive of the oral structure and is used for bench (as distinguished from in situ) construction of an oral impression tray.

3. The tray is made of a room-temperature curing plastic, usually methyl methacrylate. This involves cutting a suitable "spacer" and placing it over the positive model in the area of which an impression is required. This "spacer" insures a reasonably uniform space for the final impression material and is removed before using the tray. A handle may also be formed on the tray to facilitate handling and removal of the final impression from the oral cavity. The complete tray, which is thus a spaced negative of the positive model, is removed from the model upon completion of polymerization. It is trimmed, cleaned, separated from the spacer, and coated with an adhesive to help retain the final impression material. The tray is now ready for taking the impression.

SUMMARY OF THE INVENTION

The foregoing is a summary of prior art methods. By comparison, the present invention sets forth a "direct oral tray" procedure (intra-oral) which eliminates steps 1 and 2 of the prior art indirect (extra-oral) tray technique. This results in an appreciable saving to the dentist in both time and materials.

Briefly the system of the present invention may be described as a system for making an oral impression tray in situ including a transporter member, a tray member, and a spacer member; said transporter member comprising an arch shaped flat or curved base and a handle extending from said base, said base having a plurality of fracture lines to facilitate the selective removal of pieces of said base, said base including a plurality of apertures for the intrusion thereinto of moldable impression tray material for mechanical locking of said tray material with said transporter base, and a plurality of raised abutments on said base to establish positive bite stops relative to said base; said tray member comprising a mass of moldable polymerizable material placed on said transporter member and intruded into at least one of said apertures; said spacer member placed on said tray member and comprising a pad of uniform thickness to create a controlled space between said polymerizable material and the oral structure of the subject, and to prevent penetration of said polymerizable material into interstitial spaces between the teeth of said subject, when an oral impression is made; whereby, when said transporter, tray, and spacer system is introduced into the oral cavity of a subject, and the subject bites onto said system to the bite stops of said transporter, an oral impression tray can be formed in situ.

DRAWING

FIG. 1 is a plan view of a transporter according to this invention.

FIG. 2 is an end view of the transporter, as seen in the direction indicated by 2—2 of FIG. 1.

FIG. 3 is a plan view of a flat spacer pad.

FIG. 4 is an end view of the spacer of FIG. 3.

FIG. 5 is a plan view of a formed spacer, which is shown also in section in FIG. 5a.

DESCRIPTION-METHOD

Figure 6:
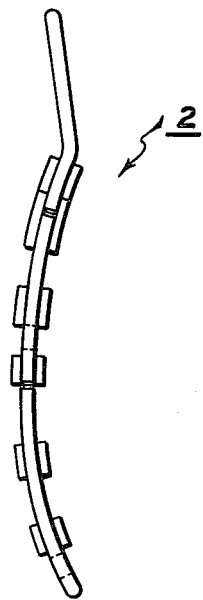
FIG. 6 is a side view of an alternative form of the transporter of FIG. 1.

The direct oral impression tray technique of this invention is carried out as follows:

1. Appropriate quantities of a two-part material system are mixed together.

2. The completed mix is then formed into a rope and placed upon a "transporter" frame.

3. A previously prepared "spacer" is then placed upon the rope of mixed material, with sufficient pressure applied to insure adhesion of the spacer to the tray material and of the tray material to the transporter frame. The tray material should be pressed sufficiently so as to intrude into locking holes in the transporter frame.

4. The assembly is carried to the mouth and centered over the area of interest. Biting pressure will form the mass of tray material to the correct thickness against stops on the transporter frame.

3. The operator then quickly finger molds the exuded tray material to form the desired lingual tray flanges and form. Muscle and cheek trimming are accomplished as in taking a normal impression to form the anterial and labial tray flanges. Within five to seven minutes of starting the mix, a completed customized impression tray is removed from the mouth.

6. The assembly is washed, trimmed and the spacer removed from the tray. This leaves a controlled space for the impression material used in the next step of the impression-taking procedure. The "spacer" not only establishes the correct space for the impression material, but also prevents the tray material from penetrating between standing teeth, thus insuring easy removal of the polymerized impression tray from the mouth.

The elimination of a "snap" impression and of the pouring of a stone model, as in the prior art method described, effects a saving of both time and material for the dentist. The direct oral tray procedure may also permit the dentist to complete taking the impressions in a single patient appointment, thus improving operating efficiency and eliminating the inconvenience of a second patient appointment.

The new tray composition has the following characteristics which make it particularly desirable as a direct oral tray material:

1. It is easily and quickly prepared at the time it is needed.
2. It is cohesive and plastic without being objectionably adhesive to the hands.
3. It is essentially odorless and tasteless.
4. It does not produce tissue burn, sting or sensation.
5. It polymerizes with very little exothermal heat or temperature rise.
6. It has low polymerization shrinkage.
7. It has adequate physical strength and toughness for taking oral impressions.
8. It leaves the mouth clean and free of residue.
9. It has an acceptable color or can be colored to facilitate placement and molding within the oral cavity.
10. The monomer or monomers are non-volatile and non-invasive to the oral tissues.

Description-Materials

The method of this invention involves the use of mono, di, tri or tetra methacrylate monomers with molecular weights in the range of 200 to 700. Resins or blends of resins within this molecular weight range will, in general, have an exothermic reaction of sufficiently low intensity (as compared to prior art monomers such as methyl methacrylate) to be useful in compositions that are intended to be polymerized in situ, against human hard or soft tissues, without causing thermal damage to the tissues. The volatility properties, viscosity characteristics and the potential biological tolerance of these resins are generally more favorable than those of lower molecular weight monomers. The polymerization of methyl methacrylate is an exothermic reaction such as would burn the tissue if done in situ. Either aromatic or aliphatic mono, di, tri or tetra functional methacrylate monomers within the molecular weight range of 200 to 700 may be useful as single monomers or as blends of monomer for specific applications.

Depending upon the product characteristics desired, various fillers may be used. Silicas, aluminas, clays, powdered metals, metal oxides, metal silicates, metal salts, plastics, organic materials and many others may be used to impart specific product characteristics, i.e., radiopacity, radiolucency, etc. electrical conductivity, control of magnetic fields, soluble ion release and other characteristics.

The filler or fillers can be utilized in a broad range of particle size distributions, from sub-micron to very coarse, singly or in blends, and with or without surface treatments to influence wetting, promote chemical bonding with the resin matrix or other special characteristics, as specific uses require. A small amount of a suitable wetting agent is used to facilitate the wetting and dispersion of the filler particles in the resin or blended resin vehicle.

The material system is suitable for a variety of dental or medically oriented uses where the material is polymerized in situ against or in close proximity to living tissues. A number of non-invasive applications can be suggested. These include, but are not limited to:

1. A direct, chairside, hard denture reline.
2. Oral splints.
3. Periodontal packs.
4. Fingernail overlay.
5. Electrical and/or magnetic shielding devices.
6. Electrical and/or magnetic focusing devices.

Products formulated within the concept of this invention may be supplied as two-part products, i.e., powder and liquid components, two-paste components, paste and liquid components, etc. A skilled formulator could convert the system to any one of the product types desired.

A specific example of the simplest product type, a powder and liquid component direct oral tray material, can be used to illustrate the invention concept:

| | | |
|---|---|---|
| a. | Resin vehicle/binder (liquid) | |
| | Ethoxylated Bis Phenol A Di Methacrylate | 98.85% |
| | Wetting agent (oleoyl sarcosine) | 1.00% |
| | 2,2$^1$-p-Tolylimino diethanol* | .15% |
| b. | Filler (powder) | |
| | Calcium carbonate, ground, average particle size 7u | 99.55% |
| | Benzoyl peroxide* | .45% |

*Subject to adjustment, as required

Mixes, comprising four to five parts of the powder with one part of the liquid, when spatulated to a cohesive mass and then rolled between the palms for 30 seconds, will produce a cohesive, plastic, moldable mass, which has excellent handling characteristics and properties, for manipulating and forming a direct oral impression tray within the oral cavity. The mix working time, or period of acceptable moldability, can be adjusted by changes in the levels of benzoyl peroxide in the powder or the 2,2$^1$-p-Tolylimino diethanol in the liquid. Normally, a working time of three to four minutes is adequate. Overall, the device can be removed from the mouth within five to seven minutes from the start of the mix.

A second example of a direct oral tray material, formulated as a two-paste product, is as follows:

Paste B (Base Paste) and Paste C (Catalyst Paste) are essentially the same composition, except the "B" paste contains an amine promoter and a coloring agent, if one is desired, while the "C" paste contains the benzoyl peroxide as a free radical polymerization initiator and preferably no coloring agent. However, the pastes may differ in composition and characteristics, if such differences are advantageous or needed.

Paste "B", the base, contains a small quantity of a suitable amine, as initiator for the free radical polymerization system, which may be selected from a variety of amines. The final choice and level of amine content will depend upon product requirements, individual preference, cost and the rate of polymerization desired. Aniline, dimethyl p toluidine, $2,2^1$ m tolyliminodiethanol, $2,2^1$-p-tolylimino diethanol or other amines may be found suitable. The selection of coloring agent will depend upon product requirements, compatibility in the formulation, toxicity restrictions and color characteristics.

Paste "C", the catalyst paste, contains a small amount of benzoyl peroxide. It is the decomposition of the benzoyl peroxide by the amine of the base paste which produces the free radicals which, in turn, initiate the polymerization of the paste vehicle monomers. Other peroxides might be substituted, but benzoyl peroxide is presently preferred.

Two-Paste Preferred Compositions:

| | |
|---|---|
| Paste "B", Base | |
| Ethoxylated Bisphenol A Di Methacrylate | 12.40% |
| BisGMA (2,2-bis)p-(2 hydroxy-$3^1$ methacryloxypropoxy phenyl) propane | 3.00% |
| Wetting Agent (i.e., oleoyl sarcosine) | 0.10% |
| $2,2^1$-p-tolyliminodiethanol | 0.15% |
| Super Flex 200 | 13.00% |
| Camel Carb | 71.35% |
| FDA Approved Color - None or As Req'd | |
| Paste "C", Catalyst | |
| Ethoxylated Bisphenol A Di Methacrylate | 12.40% |
| BisGMA | 3.00% |
| Wetting Agent (i.e., oleoyl sarcosine) | 0.10% |
| Benzoyl Peroxide | 0.10% |
| Super Flex 200, (Pfizer Minerals, Pigments and Metals Division) | 13.00% |
| Camel Carb, (Flintkote Stone Products Co.) | 71.40% |

Two resins have been selected which are blended together in one product to serve as both paste vehicle and the polymerizable binder. These resins are:

I. Ethoxylated Bisphenol A Dimethacrylate

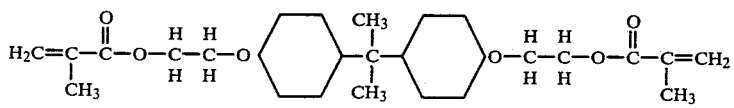

MW = 452    Viscosity at 25° C. = 1600 cps and

II. Bis GMA 2,2-bis p-(2-hydroxy-$3^1$ methacryloxypropoxy phenyl) propane

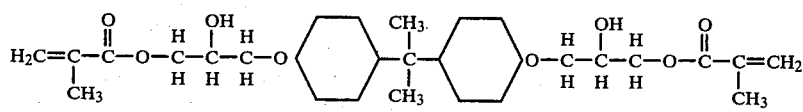

MW = 512    Viscosity at 25° C. = 1,500,000 cps

Neither resin alone has given acceptable two-paste product handling characteristics. By selectively blending the resins in the approximate ratio of four parts of I to one part of II, a paste vehicle is obtained which gives the desired balance between cohesion and adhesion properties to the formulated paste. While these two resins are the preferred combination for this particular product, the concept covers other resin combinations which might serve equally well, or even better, for other product characteristics. For example, the lower viscosity resin (I) might be replaced, in some proportion, by tri ethylene glycol dimethacrylate MW 286, trimethylolpropane, tri methacrylate MW 338, polyethylene glycol di methacrylate MW 330, 1, 3 butylene glycol di methacrylate MW 226, di ethylene glycol di methacrylate MW 330, and propoxylated Bis phenol A di methacrylate, as examples of possible substitutions. Each pair of monomers and each variation of monomer ratio will have its own characteristics, which may be preferred for a specific application. Likewise, the higher viscosity resin (II) may be replaced by di acetyl BisGMA resin, di benzoyl substituted BisGMA resin or urethane substituted BisGMA resin or other compatible high viscosity resin within the MW range of 200–700, and diluted with any of the lower viscosity resins (I) and its substituted monomers.

Description-Spacer

In the process of producing a direct oral impression tray, two functions may be fulfilled by some type of "spacer". The spacer must (1) cover the interstitial spaces between standing teeth, within the area of which the impression is required, to prevent entry therein of the impression material, and (2) provide a space within the final impression tray for the desired thickness of impression material.

The requirements for a suitable spacer are:
1. It should adapt easily and well to the oral tissues.
2. It must be compatible with the direct oral tray material.
3. It should be insoluble in saliva.
4. It should not contaminate the surface of the finalized tray, i.e., should not interfere with adhesives applied to the tray surface.
5. It should be easily removed from the final impression tray.
6. It should be cheap, as it is a disposable item.
7. It should be essentially odorless, tasteless and nontoxic.

Various materials, including rubber waxes, cloth, cellophane, plastic films, moldable clays, etc., have been evaluated for this intended use. The two most acceptable types of materials found to date are preformed foamed plastic of suitable density, hardness and thickness, and high wet strength paper of suitable thickness.

To attain the desired "space" for the final impression material within the impression tray, a thickness of approximately 2 mm is desired. A single spacer design has been found adequate for both maxillary and mandibular trays for each type of material considered. These configurations are shown in FIGS. 3, 4 and 5.

FIGS. 3 and 4 show a plan and edge view of an arch-shaped high wet strength paper or gauze spacer 20 which is moistened and placed atop a rope of tray material, which is in turn positioned on a transporter.

FIGS. 5 and 5a show a preformed plastic spacer 30, made of a soft resilient foam. Spacer 30 can most easily be described as being in the general form of an athletes mouthpiece, having a bottom 32 and front and near walls 34, 36 defining a channel 38.

Description-Transporter

The convenience, accuracy and control of producing oral tissues are greatly enhanced if the tray material is carried to the mouth, removed from the mouth and processed on a "transporter." The transporter is a generally flat or curved surface receptacle or plate, contoured to approximate the human dental arch form, made of plastic, metal or other suitable material. Its purpose is to lend convenience, stability and control to the process of placing mixed, but unset, tray forming material into the oral cavity and removing same after its polymerization. It further aids in handling the tray in the subsequent steps of impression taking and model pouring.

FIGS. 1 and 2 are plan and end views of a typical transporter according to this invention. The presently preferred transporter is a disposable transporter 2, designed such that a single unit, made in one size only, can be cut, broken or trimmed to serve a variety of impression tray making needs. In its entirety, a single unit provides support for full arch maxillary or mandibular tray impressions. Notches and/or score line 4 permit breaking the unit into right or left parts which can be used for right or left mandibular or maxillary quandrant impressions. The posterior sections 6, 8 can also be selectively removed, using only the anterior portions 16, 18 for an anterior quadrant impression tray.

Holes are provided so that the tray material can be impressed into the holes to provide mechanical locking of the impression tray to the transporter.

Raised sections 12, 1/16" in thickness, are provided as bite stops, for either maxillary or mandibular tray construction, to insure a small but adequate thickness of impression tray over the occlusal plane. Minimizing the thickness of material in this area helps insure that an adequate amount of material will be available for molding the tray flanges.

The front end portion 14 is a handle.

A reusable transporter is also contemplated. It would offer the advantages of greater strength and rigidity than the disposable plastic transporter. Such reusable transporters would probably have to be supplied in at least four configurations:
1. Full arch (maxillary or mandibular).
2. Half arch, rights (maxillary or mandibular).
3. Half arch, lefts (maxillary or mandibular).
4. Anterior arch (maxillary or mandibular).

This multiplicity of forms, with attendant costs and inventory problems, is an economic disadvantage of a reusable unit, though such reusable units might provide some cost economies over a period of time if cleanup time is not charged against them.

The function of the transporter is best understood by reviewing the procedure of making a customized oral impression tray by the direct technique. It must be appreciated that a stepwise description of any technique is only one way of achieving the final objective; some details can be altered without departing from the intent of the procedure:

1. A properly proportioned mix of the direct oral tray material is prepared according to the directions for the material selected.
2. A "rope" is formed of the mixed tray material and laid onto the transporter frame, previously trimmed to cover the area of oral structure of which an impression is required.
3. A suitable "spacer" is then pressed into the plastic, unset tray material to impress the tray material into the locking holes of the transporter frame. The basic procedure varies from this point, depending upon the type of "spacer" being used:
   (a) Soft, high drape (i.e., wet paper) spacer of the type shown in FIGS. 3, 4: The assembly transporter, with the rope of tray material and the spacer, is carried into the oral cavity and seated over the oral structure of which an impression is required. Care must be exercised to insure that the spacer covers all interstitial spaces to prevent intrusion of the tray material between the teeth. The patient is then requested to bite gently until the stops on the transporter frame are contacted. The operator then checks for proper distribution of tray material to form the required tray flanges. The tray is then formed by the operator manipulating the patient's lips and cheeks to form the labial and anterior flanges. The lingual flanges are finger molded by the operator, taking care to not disturb the completed labial and anterior flanges. Once the tray form is complete, it is held motionless until polymerization of the tray material advances to a state of strength and hardness to permit removal of the tray. This is accomplished in five to seven minutes from the start of the mix of tray material.
   (b) Preformed semi-rigid spacer of the type shown in FIGS. 5, 5A (preferred type): This type of spacer permits more of the tray to be formed outside of the oral cavity, with somewhat better control over the material distribution and greater convenience. The basic tray form can be completed by molding the prepared tray material over the convex side of the spacer before seating the assembly in the oral cavity. The semi-completed tray is then contoured to final form in the mouth. Again, the completely formed tray should be held motionless until polymerization proceeds to a point where sufficient hardness and strength are developed to safely remove the tray. This is accomplished in five to seven minutes from the start of the mix of the tray material.

The transporter provides a rigid base to carry the unset tray material conveniently into the mouth. It provides a means of controlling the thickness of the tray over the occlusal surfaces and it provides a convenient handle for removing the polymerized tray from the oral cavity. The handle also aids the operator in holding the tray in the subsequent operations of washing, trimming, removing the spacer, painting on the adhesive, filling the tray with impression material and, again, carrying the tray into the oral cavity to take the impression. Removal of the impression, cleaning and pouring the model are all facilitated by the transporter handle.

FIG. 6 shows an alternative form of transporter 2 in which the plate is generally shaped or curved to correspond to the oral cavity.

What is claimed is:

1. A system for making a custom oral impression tray in situ including a transporter member to support a body of moldable impression tray material, and a spacer member;

said transporter member comprising an arch shaped plate for extension into the oral cavity of a subject and a handle extending from said plate, said plate having a plurality of fracture lines to facilitate the selective removal of pieces of said plate, said plate including a plurality of apertures for the intrusion thereinto of moldable impression tray material for mechanical locking of said tray material with said transporter plate, and a plurality of raised abutments on said plate to establish positive bite stops relative to said plate;

said tray material comprising a mass of moldable polymerizable material placed on said transporter member and intruded into at least one of said apertures;

said spacer member placed on said tray material and comprising a pad of uniform thickness to create a controlled space between said tray material and the oral structure of the subject, and to prevent penetration of said tray material into interstitial spaces between the teeth of the subject, said transporter, tray material, and spacer system being adapted for introduction into the oral cavity of the subject for the subject to bite onto said system to the bite stops of said transporter, whereby, when said system is removed from the oral cavity and said spacer removed from said system, the resulting custom oral impression tray defines a tray cavity in the form of the oral structure of the subject with clearance space in said tray cavity to accommodate impression material for the subsequent use of said custom tray in making an oral impression.

2. A system for making a custom oral impression tray in situ including a transporter member to support both a body of moldable impression tray material and a spacer member, for conveying the same into and out of the oral cavity of a subject and for subsequent processing of said tray material to form a custom oral impression tray defining a tray cavity in the form of the oral structure of the subject with clearance space in said tray cavity to accommodate impression material for the subsequent use of said custom tray in making an oral impression, said transporter member comprising an arch shaped plate for extension into the oval cavity of the subject, and a handle extending from said plate, said plate having a plurality of fracture lines to facilitate the selective removal of pieces of said plate, said plate including a plurality of apertures for the intrusion thereinto of moldable impression tray material for mechanical locking of said tray material with said transporter plate, and a plurality of raised abutments on said plate to establish positive bite stops relative to said plate.

* * * * *